(12) United States Patent
Richard et al.

(10) Patent No.: US 6,783,272 B2
(45) Date of Patent: Aug. 31, 2004

(54) INDUCTION-HEATED DISC TRIBOMETER

(75) Inventors: Caroline Richard, Senlis (FR); Imad Sallit, Compiegne (FR); Davy Dalmas, Rueil-Malmaison (FR)

(73) Assignee: S.A.R.L. Tribolinks, Compiegne (FR)

( * ) Notice: Subject to any disclaimer, the term of this patent is extended or adjusted under 35 U.S.C. 154(b) by 0 days.

(21) Appl. No.: 10/116,356

(22) Filed: Apr. 4, 2002

(65) Prior Publication Data

US 2003/0063652 A1 Apr. 3, 2003

Related U.S. Application Data

(63) Continuation of application No. PCT/FR00/02743, filed on Oct. 3, 2000.

(30) Foreign Application Priority Data

Oct. 6, 1999 (FR) .......................................... 99 12462

(51) Int. Cl.$^7$ ............................. G01N 3/22; G01N 3/02
(52) U.S. Cl. ............................. 374/41; 374/48; 374/50; 374/153; 73/846; 219/600
(58) Field of Search .............................. 73/9, 843–848; 374/141, 153, 121, 45–46, 48, 50; 219/600

(56) References Cited

U.S. PATENT DOCUMENTS

| | | | | |
|---|---|---|---|---|
| 3,535,914 A | * | 10/1970 | Mehrbrodt et al. ........... | 374/46 |
| 4,173,142 A | * | 11/1979 | Heinz | |
| 4,584,882 A | * | 4/1986 | Tosaki | |
| 4,878,379 A | * | 11/1989 | Deer | |
| 4,914,958 A | | 4/1990 | van Damme | |
| 5,038,601 A | * | 8/1991 | Renneker | |
| 5,079,956 A | * | 1/1992 | Burhin et al. | |
| 5,163,317 A | * | 11/1992 | Ono et al. | |
| 5,187,987 A | * | 2/1993 | Anderson et al. ............. | 73/852 |
| 5,221,713 A | * | 6/1993 | Kempner et al. | |
| 5,795,990 A | * | 8/1998 | Gitis et al. | |
| 5,921,148 A | * | 7/1999 | Howell | |
| 6,070,457 A | * | 6/2000 | Robinson | |
| 6,164,818 A | * | 12/2000 | Dick et al. | |
| 6,401,058 B1 | * | 6/2002 | Akalin et al. | |
| 6,418,776 B1 | * | 7/2002 | Gitis et al. | |
| 6,666,066 B1 | * | 12/2003 | Mollenhauer et al. ........... | 73/9 |
| 2003/0033860 A1 | * | 2/2003 | Hajduk et al. ............. | 73/54.37 |
| 2003/0194900 A1 | * | 10/2003 | Lee ............................. | 439/358 |

FOREIGN PATENT DOCUMENTS

| | | | |
|---|---|---|---|
| FR | 2 685 774 A | | 7/1993 |
| GB | 2 232 091 A | | 12/1990 |
| JP | 55093049 A | * | 7/1980 |
| JP | 58028656 A | * | 2/1983 |
| JP | 62 278427 | | 12/1987 |
| JP | 02201138 A | * | 8/1990 |
| JP | 06221990 A | * | 8/1994 |
| JP | 06 281563 | | 10/1994 |
| JP | 07 113735 | | 5/1995 |
| JP | 10 026581 | | 1/1998 |

OTHER PUBLICATIONS

Jean–Yves Catherin, *La Tribologie se Renouvelle à Chaque Application*, Mesures Regulation Automatisme, Fr, CFE. Paris, No. 687, Sep. 1, 1996, pp. 61–63.

\* cited by examiner

*Primary Examiner*—Gail Verbitsky
(74) *Attorney, Agent, or Firm*—Piper Rudnick LLP

(57) ABSTRACT

A disc tribometer for measuring tribological, mechanical and thermal phenomena including at least a first rotary support for receiving a test sample, a second rotary support for receiving a second test sample, means for measuring torque applied to each of the supports, and at least one induction coil positioned to heat one of the test samples.

16 Claims, 1 Drawing Sheet

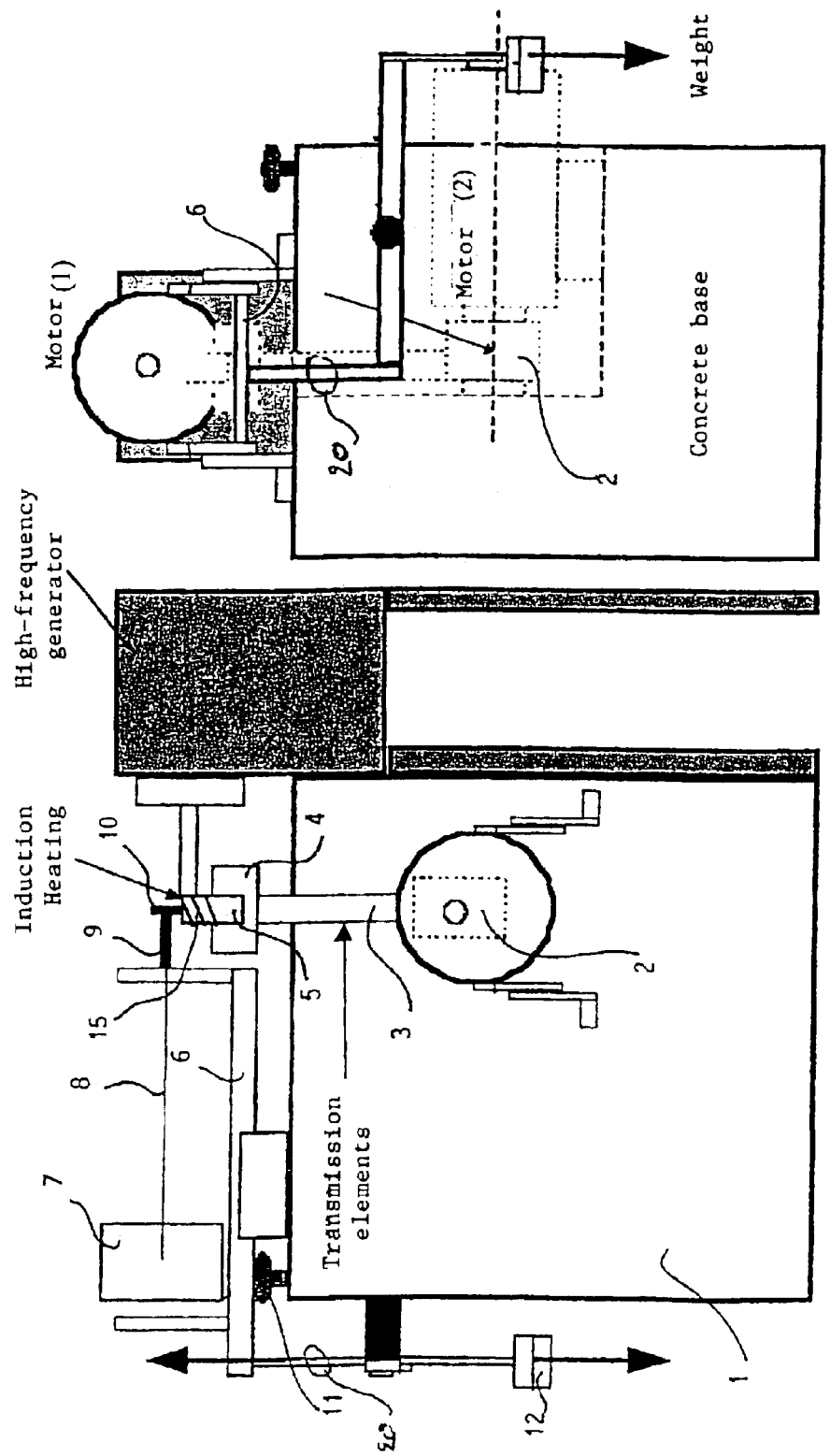

INDUCTION-HEATED DISC TRIBOMETER

RELATED APPLICATION

This is a continuation of International Application No. PCT/FR00/02743, with an international filing date of Oct. 3, 2000, which is based on French Patent Application No. 99/12462, filed Oct. 6, 1999.

FIELD OF THE INVENTION

The present invention concerns the field of metrology equipment and more particularly tribometers.

BACKGROUND

Metrology equipment is intended for the measurement of the mechanical, tribological and thermal phenomena produced between two bodies rubbing against each other as well as the influence of materials interposed between two bodies in relative movement.

The general principle of such devices is well known. For example, the tribometer described in French patent FR 2,660,756 which concerns a device for improvement of the evaluation of lubricant performance. This device makes it possible to load a mobile piece on a fixed piece in punctiform, linear or surface contact in the presence of a lubricant. A jackscrew acts on one of the pieces in contact. Force sensors measure the force applied.

Another French patent FR 2,685,774 describes a device comprising a fixed assembly formed by a caisson and a first vertical electric spindle driving a first disc. A mobile assembly comprises a second caisson supporting a second electric spindle which can pivot around an articulation axis. Other tribometers are described in Japanese patents JP 1006581, JP 06281563 and JP 62278427, British patent GB 2,232,091 and American patent U.S. Pat. No. 4,914,958.

Certain measurements require the regulation of the temperature of one or both test samples in contact. In order to do this, it is known to heat the test samples before they are placed on the driving supports.

The problem posed is that of precise control of the temperature and that of maintaining a temperature differential between the two test samples in contact.

Known in the state of the art is Japanese patent JP 07113735. This document pertains to the use of an induction coil not for heating one of the test samples during a tribometer test period but for denaturing the material by heating and cooling cycles. Such an application is not satisfactory with regard to the measurements generally performed in tribometry.

SUMMARY OF THE INVENTION

The invention proposes a solution to this problem which enables creation of an improved tribometer.

This invention relates to a disc tribometer for measuring tribological, mechanical and thermal phenomena including at least a first rotary support for receiving a test sample, a second rotary support for receiving a second test sample, means for measuring torque applied to each of said supports, and at least one induction coil positioned to heat one of the test samples.

BRIEF DESCRIPTION OF THE DRAWINGS

Better understanding of the invention will be obtained by reading the description below with refference to a nonlimitative example of implementation in which:

FIG. 1 represents a side view of a tribometer according to the invention, and

FIG. 2 represents a front view of said tribometer.

DETAILED DESCRIPTION

In its most general sense, the invention concerns a disc tribometer for measuring tribological, mechanical and thermal phenomena comprising at least a first rotary support for receiving a test sample and a second rotary support for receiving a second test sample, as well as means for measuring the torque applied to each of said supports, characterized in that it further comprises at least one induction coil positioned so as to enable heating of the rotating test samples. The heating is controlled so as to assure an essentially constant temperature during the tribological parameter measurement phase for the entire duration of the measurement. The heating can also be controlled according to a time-based evolution curve over a range of time corresponding to the duration of the measurement.

According to a first variant, the tribometer comprises an induction coil intended to enable the heating of only one of the rotating test samples.

According to a second variant, the tribometer comprises two independent induction coils, each one being intended to enable the heating of only one of the test samples.

A tribometer according to the invention makes it possible to precisely regulate the temperature of one of the test samples without disturbing the measurement process. The induction coil is advantageously coaxial with one of the rotary supports.

According to a preferred variant, the tribometer according to the invention furthermore comprises a pyrometer positioned so as to record the thermal radiation produced at the interface of the two test samples.

The tribometer advantageously comprises an enclosure surrounding the rotary supports, said enclosure being connected to a system for controlling the atmosphere.

According to an advantageous variant, at lease one of the rotary supports is driven by a motor supported by a platform equilibrated by an adjustable weight and in that it comprises a sensor for measuring the instantaneous force applied by said weight.

Turning now to the drawings, FIGS. 1 and 2 represent schematic views of a device according to the invention.

The device according to the described example comprises a frame (1) supporting a first motor (2) driving a shaft (3) causing rotation of a platform (4) comprising a mandrel for receiving a first test sample (5). This motor (2) is equipped with a speed and/or position sensor as well as a power sensor measuring the electromotive or counter-electromotive force applied to the platform (4).

The device comprises a second motorized assembly constituted by a plate (6) supporting a second motor (7) driving a second shaft (8) perpendicular to the first shaft (3). This assembly drives a second plate (9) equipped with a mandrel that can receive a second test sample (10) which can be brought into linear or punctiform contact with the first test sample (5).

The two test samples are driven in relative rotation according to perpendicular axes of rotation at speeds assuring a sliding or, to the contrary, at identical speeds assuring contact without sliding. The induction coil is oriented according to an axis corresponding to the axis of rotation of one of the test samples. In the case in which two induction coils are used, the axes of the two coils will be perpendicular with each one corresponding to the axis of rotation of one of the test samples.

The plate (6) is mounted in a tiltable manner in relation to a pivot (11) perpendicular to the two shafts (3, 8). A weight (12) allows adjustment of the supporting force of the second test sample (10) on the platform (4).

The device comprises an extensometer (20) or a force sensor enabling measurement of the instantaneous force applied to the test sample. This force is not constant and varies notably in relation to the inertia of the system.

The two test samples are driven in a manner so as to create a controllable friction zone. The measurement parameters enable analysis of the tribological phenomena of the materials constituting the test samples and possibly of the lubrication materials introduced between the test samples.

An indicator is constituted by the result of a function of the normal force applied to a test sample and the measured tangential force.

In order to enable measurements taking into account the incidence of the temperature, the device furthermore comprises a high-frequency generator (14) powering an induction coil (15).

This induction coil surrounds one of the test samples (10) and provides for its temperature modification and regulation. The coil does not come into contact with the test samples and therefore does not disturb the measurement.

According to one mode of implementation, the thermoregulation process consists of maintaining a constant temperature of only one of the test samples. In another variant, the two test samples are maintained at different constant temperatures for measuring the effect of a temperature differential. Two pyrometers are provided in this case so as to enable independent measurement of the temperature of each of the test samples.

The heating temperature are comprised between 600 and 1200° C. for certain applications.

The induction coil is formed by a winding of several spirals, 6 in the example described, of copper wire of 3 mm section. The spirals present a section of 500 mm so as to enable the positioning of a test sample with a maximum section of 450 mm. It is obvious that the dimensions of the coil can be modified by the expert in the field so as to respond to the measurement requirements.

The high-frequency generator delivers an electric signal of 30 to 300 kHz at a power of 25 kilowatts.

The assembly formed by the test sample supports, the test samples and the induction coil can be inserted into an enclosure that is closed in a tight manner, presenting passages for the shafts, so as to allow control of the atmosphere.

The device also comprises an infrared pyrometer and/or thermocouples measuring the temperature of the contact zone.

The data concerning the torque forces and absorbed power, the tangential force exerted by the second test sample on the first test sample, in relation to the weight (12), the heating power, the measured temperature and possibly other parameters are processed by a calculator for determination of a coefficient of friction of the pair of test samples.

Different variants of implementation of the invention are possible. The device can comprise an induction coil for each of the test samples or a cooled support. It can also comprise a filtration system enabling continuous analysis of wear debris in lubrication mode.

The device can also comprise an additional sample holder for heating test samples made of nonconductive material. The sample holder would be constituted in this case by a container made of an electrically conductive material designed to receive the test sample and to transmit to it the mechanical as well as thermal stress. This sample holder interlocks with one of the rotary supports so as to make it possible to process a test sample made of an insulating or weakly conductive material.

The rotary supports can be parallel or perpendicular. If they are perpendicular, it is advantageous if one of the supports is horizontal so as prevent the loss of debris which must be taken into account in tribological phenomena.

The speeds of the two supports can be identical (i.e., speeds enabling movement of the two test samples without sliding) or different, and one of the supports can exhibit a zero rate of rotation.

What is claimed is:

1. A disc tribometer for measuring tribological, mechanical and thermal phenomena comprising:
   at least a first rotary support for receiving a first test sample;
   a second rotary support for receiving a second test sample;
   means for measuring torque applied to each of said supports; and
   at least one induction coil positioned to heat one of the samples, wherein one of the rotary supports is driven by a motor supported by a platform equilibrated by an adjustable weight and further comprises a sensor for measuring instantaneous force applied by said weight.

2. The tribometer according to claim 1, wherein the induction coil is coaxial with one of the rotary supports.

3. The tribometer according to claim 1 or 2, further comprising a pyrometer positioned to record thermal radiation produced at an interface of the test samples.

4. The tribometer according to claim 1, wherein heating is maintained essentially constant during one measurement cycle.

5. The tribometer according to claim 1, wherein at least one of the supports is cooled.

6. The tribometer according to claim 1, further comprising a sample holder made of a conductive material.

7. The tribometer according to claim 1, wherein the induction coil surrounds only one of the test samples.

8. The tribometer according to claim 1, wherein the rotary supports turn at different speeds.

9. The tribometer according to claim 1, wherein one of the supports is fixed.

10. The tribometer according to claim 1, wherein one of the supports is horizontal.

11. The tribometer according to claim 1, isolated from the external atmosphere and connected to a system for controlling the atmosphere within the tribometer.

12. A disc tribometer for measuring tribological, mechanical and thermal phenomena comprising:
    at least a first rotary support for receiving a first test sample;
    a second rotary support for receiving a second test sample;
    means for measuring torque applied to each of said supports;
    at least one induction coil positioned to heat one of the samples; and
    another induction coil for differential heating of another of the test samples.

13. A disc tribometer for measuring tribological, mechanical and thermal phenomena comprising:

at least a first rotary support for receiving a first test sample;

a second rotary support for receiving a second test sample;

means for measuring torque applied to each of said supports;

at least one induction coil positioned to heat one of the samples; and a filtration system enabling continuous analysis of wear debris.

14. A disc tribometer for measuring tribological, mechanical and thermal phenomena comprising:

at least a first rotary support for receiving a first test sample;

a second rotary support for receiving a second test sample, wherein the first rotary support has a first motorized assembly driving the first rotary support with a shaft and the second rotary support has a second motorized assembly including a plate supporting a second motor driving a second shaft perpendicular to the first shaft;

means for measuring torque applied to each of said supports; and at least one induction coil positioned to heat one of the samples.

15. The tribometer according to claim 14, wherein the second assembly drives a second plate equipped with a mandrel that receives a second test sample brought into linear or punctiform contact with the first test sample.

16. A disc tribometer for measuring tribological, mechanical and thermal phenomena comprising:

at least a first rotary support for receiving a first test sample;

a second rotary support for receiving a second test sample, wherein the rotary supports turn at identical speeds;

means for measuring torque applied to each of said supports; and at least one induction coil positioned to heat one of the samples.

* * * * *